United States Patent
Sawyer et al.

(10) Patent No.: US 7,485,749 B2
(45) Date of Patent: *Feb. 3, 2009

(54) PREPARATION OF ACETIC ACID

(75) Inventors: Gary A. Sawyer, Media, PA (US); Wayne J. Brtko, Glen Mills, PA (US); Ronnie M. Hanes, Crofton, MD (US); Brian A. Salisbury, Oxford, PA (US)

(73) Assignees: Lyondell Chemical Technology, L.P., Greenville, DE (US); Millennium Petrochemicals inc., Houston, TX (US)

( * ) Notice: Subject to any disclaimer, the term of this patent is extended or adjusted under 35 U.S.C. 154(b) by 219 days.

This patent is subject to a terminal disclaimer.

(21) Appl. No.: 11/508,109

(22) Filed: Aug. 22, 2006

(65) Prior Publication Data

US 2008/0051601 A1    Feb. 28, 2008

(51) Int. Cl.
*C07C 51/42* (2006.01)

(52) U.S. Cl. .................................................... 562/608
(58) Field of Classification Search ............... 562/608
See application file for complete search history.

(56) References Cited

U.S. PATENT DOCUMENTS

| | | | |
|---|---|---|---|
| 3,769,329 A | 10/1973 | Paulik et al. | 260/488 K |
| 5,155,265 A | 10/1992 | Scates et al. | 562/608 |
| 5,155,266 A | 10/1992 | Scates et al. | 562/608 |
| 5,202,481 A | 4/1993 | Scates et al. | 562/608 |
| 5,371,286 A | 12/1994 | Blay et al. | 562/519 |
| 5,387,713 A | 2/1995 | Cook et al. | 562/608 |
| 5,416,237 A | 5/1995 | Aubigne et al. | 562/519 |
| 5,620,567 A | 4/1997 | Seidel et al. | |
| 5,625,095 A | 4/1997 | Miura et al. | 562/519 |
| 5,783,731 A | 7/1998 | Fisher et al. | 562/519 |
| 5,817,869 A | 10/1998 | Hinnenkamp et al. | 562/519 |
| 5,932,764 A | 8/1999 | Morris et al. | 562/519 |
| 6,232,491 B1 | 5/2001 | Cunnington et al. | 560/248 |
| 6,323,364 B1 | 11/2001 | Agrawal et al. | 562/519 |
| 6,339,171 B1 | 1/2002 | Singh et al. | 562/519 |
| 6,667,418 B2 | 12/2003 | Broussard et al. | 562/519 |
| 2003/0199711 A1 | 10/2003 | Broussard et al. | 562/519 |

FOREIGN PATENT DOCUMENTS

| | | |
|---|---|---|
| EP | 0085898 | 8/1983 |
| EP | 0322215 | 6/1989 |
| WO | PCT/US2007/017562 | 1/2008 |

OTHER PUBLICATIONS

Michael B. Smith, "Organic Synthesis: Theory, Reactions, and Methods" 1994, *McGraw Hill, Inc., U.S.A.*, XP-002462909, pp. 655-656.

*Primary Examiner*—Taylor Victor Oh
(74) *Attorney, Agent, or Firm*—Shao-Hua Guo

(57) ABSTRACT

A method for removing aldehyde impurities from an acetic acid stream is disclosed. The method comprises reacting aldehyde impurities with a hydroxyl compound in a drying distillation column or a combined column to form corresponding acetals. The acetals are subsequently removed as heavy impurities from acetic acid by distillation.

24 Claims, No Drawings

PREPARATION OF ACETIC ACID

FIELD OF THE INVENTION

The invention relates to preparation of acetic acid. More particularly, the invention relates to a method for removing aldehyde impurities from acetic acid.

BACKGROUND OF THE INVENTION

The carbonylation of methanol produces acetic acid:

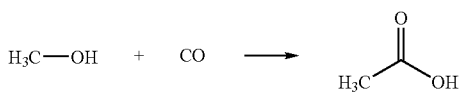

Prior to 1970, acetic acid was made using cobalt catalysts. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One problem with the original Monsanto process is that a large amount of water (about 14%) is needed to produce hydrogen in the reactor via the water-gas shift reaction ($CO + H_2O = CO_2 + H_2$). Water and hydrogen are needed to react with precipitated Rh(III) and inactive $[RhI_4(CO)_2]^-$ to regenerate the active Rh(I) catalyst. The large amount of water increases the amount of hydrogen iodide, which is highly corrosive and leads to engineering problems. Further, removing a large amount of water from the acetic acid product is costly.

In the late '70s, Celanese modified the Monsanto process by adding lithium iodide salt to the carbonylation. Lithium iodide salt increases the catalyst stability by minimizing the side reactions that produce inactive Rh(III) species and therefore the amount of water needed is reduced. However, the high concentration of lithium iodide salt promotes stress crack corrosion of the reactor vessels. Furthermore, the use of iodide salts increases the iodide impurities in the acetic acid product.

In the late '90s, Lyondell Chemical Company (by its predecessors) developed a new rhodium carbonylation catalyst system that does not use iodide salt. The catalyst system uses a pentavalent Group VA oxide such as triphenylphosphine oxide as a catalyst stabilizer. The Lyondell catalyst system not only reduces the amount of water needed but also increases the carbonylation rate and acetic acid yield. See U.S. Pat. No. 5,817,869.

One challenge still facing the industry is that lowering water concentration in the methanol carbonylation results in increased aldehyde formation. Methods for reducing aldehyde concentration in acetic acid are known. For instance, U.S. Pat. No. 6,667,418 discloses a method for reducing aldehydes by oxidizing them with air, hydrogen peroxide and other free radical initiators in an integrated acetic acid production process at an elevated temperature. Introducing free radical initiators into acetic acid production process is inconvenient because free radical initiators are explosive.

New method for reducing aldehydes in acetic acid is needed. Ideally, the method could be performed conveniently and safely.

SUMMARY OF THE INVENTION

The invention is a method for the preparation of acetic acid. The method comprises reacting methanol and carbon monoxide in the presence of a carbonylation catalyst, a catalyst stabilizer, methyl iodide, water and methyl acetate to produce an acetic acid stream. At least a portion of the acetic acid stream is flashed to produce a vapor stream comprising acetic acid, water, methyl acetate, methyl iodide and impurities including an aldehyde impurity, and a liquid stream comprising the catalyst and the catalyst stabilizer. The vapor stream is separated using a distillation column into an acetic acid product stream comprising acetic acid, heavy impurities including the aldehyde impurity, and a minor amount of water, and an overhead stream comprising methyl iodide, water, methanol, methyl acetate and acetic acid. The acetic acid product stream and a hydroxyl compound are fed into a distillation column wherein the aldehyde impurity reacts with the hydroxyl compound to form an acetal, and wherein the water is removed from a top portion of the distillation column and an essentially anhydrous acetic acid product stream comprising acetic acid and heavy impurities including the acetal is taken from a bottom portion of the distillation column. The acetal and other heavy impurities are then separated from the acetic acid by distillation.

Alternatively, the vapor stream from the flash separation and a hydroxyl compound are fed into a so called "combined" column. The aldehyde impurity reacts with the hydroxyl compound to form acetal in the combined column. A light stream, an essentially anhydrous acetic acid product stream, and a heavy stream are separated by the combined column. The acetal, which stays either in the essentially anhydrous acetic acid product stream or in the heavy stream, is subjected to further removal by, e.g., distillation.

DETAILED DESCRIPTION OF THE INVENTION

An acetic acid stream containing aldehyde impurities is produced by methanol carbonylation. The carbonylation reaction is performed in the presence of a carbonylation catalyst and a catalyst stabilizer. Suitable carbonylation catalysts include those known in the acetic acid industry. Examples of suitable carbonylation catalysts include rhodium catalysts and iridium catalysts.

Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof.

Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H+$, $[Ir(CH_3)I_3(CO)_2]^-H+$, $Ir_4(CO)_{12}$, $IrCl_3 \cdot 4H_2O$, $IrBr_3 4H_2O$, $Ir_3(CO)_{12}$, $Ir_2O_3$, $IrO_2$, $Ir(acac)(CO)_2$, $Ir(acac)_3$, $Ir(Ac)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are chloride-free compounds such as acetates.

Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817,869. Phosphine oxides are more preferred. Triphenylphosphine oxides are most preferred.

The carbonylation reaction is performed in the presence of water. Preferably, the concentration of water present is from about 2 wt % to about 14 wt % based on the total weight of the reaction medium. More preferably, the water concentration is from about 2 wt % to about 10 wt %. Most preferably, the water concentration is from about 4 wt % to about 8 wt %.

The reaction is performed in the presence of methyl acetate. Methyl acetate can be formed in situ. If desirable, methyl acetate can be added as a starting material to the reaction mixture. Preferably, the concentration of methyl acetate is from about 2 wt % to about 20 wt % based on the total weight of the reaction medium. More preferably, the concentration of methyl acetate is from about 2 wt % to about 16 wt %. Most preferably, the concentration of methyl acetate is from about 2 wt % to about 8 wt %.

The reaction is performed in the presence of methyl iodide. Methyl iodide is a catalyst promoter. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Hydrogen may also be fed into the reactor. Addition of hydrogen can enhance the carbonylation efficiency. Preferably, the concentration of hydrogen is from about 0.1 mol % to about 5 mol % of carbon monoxide in the reactor. More preferably, the concentration of hydrogen is from about 0.3 mol % to about 3 mol % of carbon monoxide in the reactor.

Methanol and carbon monoxide are fed to the carbonylation reactor. The methanol feed to the carbonylation reaction can come from a syngas-methanol facility or any other source. Methanol does not react directly with carbon monoxide to form acetic acid. It is converted to methyl iodide by its reaction with hydrogen iodide. Methyl iodide then reacts with carbon monoxide and water to give acetic acid and to regenerate the hydrogen iodide. Carbon monoxide not only becomes part of the acetic acid molecule, but it also plays an important role in the formation and stability of the active catalyst.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 2,000 psig. More preferably, the reaction is performed under a pressure within the range of about 300 psig to about 500 psig.

At least a portion of the acetic acid stream is withdrawn from the reactor and is separated, by a flash separation, into a liquid stream comprising the majority of the catalyst and the majority of the catalyst stabilizer and a vapor stream comprising acetic acid, the reactants, water, methyl iodide, and impurities generated during the carbonylation reaction including aldehydes. The liquid stream is then optionally recycled to the carbonylation reactor. The vapor stream is passed to a distillation column.

The distillation column, so called "light-ends distillation," separates an overhead comprising methyl iodide, water, and methyl acetate from an acetic acid product stream comprising acetic acid, water, and heavy impurities including the aldehyde impurity. The overhead from the light-ends distillation preferably is condensed and separated in a decanter to a light, aqueous phase and a heavy, organic phase. The heavy, organic phase comprises a major portion of methyl iodide. The light, aqueous phase comprises water, acetic acid, and methyl acetate. The heavy phase may be recycled to the carbonylation reactor. The light, aqueous phase may be recycled to the carbonylation reactor or to the light-ends distillation column.

Conventionally, the acetic acid product stream from the light-ends distillation column is passed to a so called "drying column" to remove water and then subjected to a so called "heavy-ends distillation" to remove the heavy impurities such as propionic acid.

According to the invention, a hydroxyl compound is also fed into the drying column wherein the aldehyde impurity reacts with the hydroxyl compound to form an acetal. The hydroxyl compound can be premixed with the acetic acid product stream and the mixture is then fed into the drying column. Alternatively, the hydroxyl compound is fed into the drying column separately. The water is removed from a top portion of the drying column and an essentially anhydrous acetic acid that contains the acetal and other heavy impurities is taken from a bottom portion of the drying column. The acetal and other heavy impurities are removed from the acetic acid by heavy-ends distillation.

According to the invention, the reaction of the hydroxyl compound with the aldehyde impurity can also be carried out in a so called "combined column." A combined column is a distillation column which has both the function of the light-ends distillation and the function of the drying column. By this method, a vapor stream from the flash separation and a hydroxyl compound are fed into the combined column; the vapor stream and the hydroxyl compound can be either premixed or fed as separate streams.

The combined column may vary in the diameter/height ratio and the number of stages according to the composition of vapor stream from the flash separation and the requisite product quality. For instance, U.S. Pat. No. 5,416,237, the teachings of which are incorporated herein by reference, discloses a combined column. The vapor stream from the flash separation and the hydroxyl compound are preferably fed into the combined column from the low portion of the column, for instance about 3 to 8 stages above the bottom of the column. A light stream, which comprises water, methyl iodide, and methyl acetate, is taken from a top portion of the combined column. The light stream may return to the carbonylation reaction with or without further separation. An essentially anhydrous (containing less than 1000 ppm of water) acetic acid product stream is taken from a middle portion of the column, for instance, about 10-20 stages above the feed of the vapor stream from the flash separation and the hydroxyl compound. A heavy stream, which may comprise the catalyst and the catalyst stabilizer carried over from the flash separation, is taken from a bottom portion of the column.

The acetal formed by the reaction of aldehyde and hydroxyl compound may stay either in the essentially anhydrous acetic acid product stream or in the heavy stream, or both. The essentially anhydrous acetic acid product containing the acetal and other heavy impurities such as propionic acid is further purified by heavy-ends distillation as discussed above. The heavy stream containing the acetal may be treated as a waste stream for disposal. Alternatively, the heavy stream may be subjected to purification to remove acetal. The purified heavy stream may then be recycled to the carbonylation reaction.

A combined column is particularly useful when the water concentration in the carbonylation is low, for instance, 6% or lower based on the total weight of the carbonylation reaction medium.

When the reaction of the aldehyde impurity and the hydroxyl compound is carried out in the drying column, the method of the invention is preferably used for removing "heavy" aldehyde impurities. By "heavy," we mean that the aldehyde impurities have relatively high boiling points and stay in the acetic acid product stream after the light-ends distillation. Preferably, the heavy aldehyde impurity has a boiling point of about 75° C. or higher. More preferably, the aldehyde impurity has a boiling point that is close to the boiling point of acetic acid (118° C.). Such impurities are otherwise difficult to remove from the acetic acid product by distillation. This invention provides an efficient way to remove these aldehyde impurities by their reaction with hydroxyl compounds to form acetals that have higher boiling points than acetic acid. The acetals are then removed from acetic acid by distillation. Examples of such heavy aldehyde impurities include crotonaldehyde, butyraldehyde, their derivatives such as 2-ethyl crotonaldehyde, 2-ethyl butyraldehyde, the like, and mixtures thereof.

When the reaction of the aldehyde impurity and the hydroxyl compound is carried out in the combined column, the method of the invention is suitable for removing the above discussed heavy aldehyde impurities and light aldehyde impurities such as acetaldehyde.

Suitable hydroxyl compounds for reacting with the aldehydes include alcohols, glycols, and polyols. Suitable alcohols include $C_4$ to $C_{10}$ alcohols. Sterically bulky alcohols, such as 2-ethylhexan-1-ol, 2-methylhexan-2-ol, 3-methylpentan-3-ol, 2-methylpentan-2-ol, 2-methylbutan-2-ol, and 3-methyl-butan-2-ol, are preferred. Suitable glycols include 2-methyl-1,3-propanediol, ethylene glycol, 1,2-propylene glycol, 1,3-propylene glycol, 1,2-butanediol, 1,3-butanediol, 1,5-pentanediol, 1,6-hexanediol, 2,2-dimethyl-1,3-propanediol, cyclohexane-1,4-dimethanol, and neopentyl glycol, the like, and mixtures thereof. Suitable polyols include those which have three or more hydroxyl functional groups such as glycerin. Glycols are preferred because they form stable cyclic acetals with aldehydes. Ethylene glycol and 2-methyl-1,3-propanediol are most preferred because they are inexpensive and readily available.

Preferably, the hydroxyl compound is used in an amount within the range of about 0.1 equivalent to about 10 equivalents of the aldehyde impurities. More preferably, the hydroxyl compound is used in an amount within the range of about 1 equivalent to about 5 equivalents of the aldehyde impurities.

Preferably, the reaction of the aldehyde impurity with the hydroxyl compound is performed in the presence of a mineral acid. Suitable mineral acids include hydrochloric acid, hydriodic acid, nitric acid, phosphoric acid, sulfuric acid, the like, and mixtures thereof. The amount of mineral acid used depends on the reaction conditions. Usually, the mineral acid is used in an amount less than 1%, preferably less than 1000 ppm, and more preferably less than 100 ppm, of the total weight of the reaction medium.

The following examples merely illustrate the invention. Those skilled in the art will recognize many variations that are within the spirit of the invention and scope of the claims.

EXAMPLE 1

A solution (50 g), which contains 91.9 wt % of acetic acid, 8.0 wt % of water, and 400 ppm of acetaldehyde, is prepared and loaded into a 100 mL round bottom flask. To the flask are added 0.1 mL of toluene as an internal standard, 125 mg (3 equivalents) of 2-methyl-1,3-propanediol. The resulting solution is stirred for 1 minute to ensure adequate mixing and 21 μL of a 57% solution of hydriodic acid is added to it via syringe. The solution is then stirred at room temperature (about 25° C.) for 30 minutes, at which time a GC aliquot is obtained and analyzed. The GC analysis indicates that 36.7% of the acetaldehyde is converted to its 2-methyl-1,3-propanediol acetal.

EXAMPLE 2

A solution (50 g), which contains 95.9 wt % of acetic acid, 4.0 wt % of water, and 400 ppm of acetaldehyde, is prepared and loaded into a 100 mL round bottom flask. To the flask are added 0.1 mL of toluene as an internal standard, 125 mg (3 equivalents) of 2-methyl-1,3-propanediol. The resulting solution is stirred for 1 minute to ensure adequate mixing and 21 μL of a 57% solution of hydriodic acid is added to it via syringe. The solution is then stirred at room temperature for 30 minutes, at which time a GC aliquot is obtained and analyzed. The GC analysis indicates that 66.7% of the acetaldehyde is converted to its 2-methyl-1,3-propanediol acetal.

EXAMPLE 3

A solution (50 g), which contains 97.9 wt % of acetic acid, 2.0 wt % of water, and 400 ppm of acetaldehyde, is prepared and loaded into a 100 mL round bottom flask. To the flask are added 0.1 mL of toluene as an internal standard, 125 mg (3 equivalents) of 2-methyl-1,3-propanediol. The resulting solution is stirred for 1 minute to ensure adequate mixing and 21 μL of a 57% solution of hydriodic acid is added to it via syringe. The solution is then stirred at room temperature for 30 minutes, at which time a GC aliquot is obtained and analyzed. The GC analysis indicates that 68.2% of the acetaldehyde is converted to its 2-methyl-1,3-propanediol acetal.

EXAMPLE 4

A solution (50 g), which contains 98.9 wt % of acetic acid, 1.0 wt % of water, and 400 ppm of acetaldehyde is prepared and loaded into a 100 mL round bottom flask. To the flask are added 0.1 mL of toluene as an internal standard, 125 mg (3 equivalents) of 2-methyl-1,3-propanediol. The resulting solution is stirred for 1 minute to ensure adequate mixing and 21 μL of a 57% solution of hydriodic acid is added to it via syringe. The solution is then stirred at room temperature for 30 minutes, at which time a GC aliquot is obtained and analyzed. The GC analysis indicates that 81.2% of the acetaldehyde is converted to its 2-methyl-1,3-propanediol acetal.

EXAMPLE 5

A solution (50 g), which contains 99.9 wt % of acetic acid and 400 ppm of acetaldehyde, is prepared and loaded into a 100 mL round bottom flask. To the flask are added 0.1 mL of toluene as an internal standard, 125 mg (3 equivalents) of 2-methyl-1,3-propanediol. The resulting solution is stirred for 1 minute to ensure adequate mixing and 21 μL of a 57% solution of hydriodic acid is added to it via syringe. The solution is then stirred at room temperature for 30 minutes, at which time a GC aliquot is obtained and analyzed. The GC analysis indicates that 100% of the acetaldehyde is converted to its 2-methyl-1,3-propanediol acetal.

EXAMPLE 6

A solution (50 g), which contains 97.9 wt % of acetic acid, 2.0 wt % of water, and 400 ppm acetaldehyde, is prepared and loaded into a 100 mL round bottom flask. To the flask are added 0.1 mL of toluene as an internal standard, 41 mg (1 equivalent) of 2-methyl-1,3-propanediol. The resulting solution is stirred for 1 minute to ensure adequate mixing and 21 μL of a 57% solution of hydriodic acid is added to it via syringe. The solution is then stirred at room temperature for 30 minutes, at which time a GC aliquot is obtained and analyzed. The GC analysis indicates that 53.7% of the acetaldehyde is converted to its 2-methyl-1,3-propanediol acetal.

EXAMPLE 7

A solution (50 g), which contains 97.9 wt % of acetic acid, 2.0 wt % of water, and 400 ppm of acetaldehyde, is prepared and loaded into a 100 mL round bottom flask. To the flask are added 0.1 mL of toluene as an internal standard, 125 mg (3 equivalents) of 2-methyl-1,3-propanediol. The resulting solution is stirred for 1 minute to ensure adequate mixing and 3 μL (50 ppm) of a 57% solution of hydriodic acid is added to it via syringe. The solution is then stirred at room temperature for 30 minutes, at which time a GC aliquot is obtained and analyzed. The GC analysis indicates that 100% of the acetaldehyde is converted to its 2-methyl-1,3-propanediol acetal.

EXAMPLE 8

A solution (50 g), which contains 99.9 wt % of acetic acid and 400 ppm of 2-ethylcrotonaldehyde, is prepared and loaded into a 100 mL round bottom flask. To the flask are added 0.1 mL of toluene as an internal standard, 92 mg (5 equivalents) of 2-methyl-1,3-propanediol. The resulting solution is stirred for 1 minute to ensure adequate mixing and 21 μL of a 57% solution of hydriodic acid is added to it via syringe. The solution is then stirred at room temperature for 30 minutes, at which time a GC aliquot is obtained and analyzed. The GC analysis indicates that 40% of the 2-ethylcrotonaldehyde is converted to its 2-methyl-1,3-propanediol acetal.

We claim:
1. A method for producing acetic acid, said method comprising:
(a) reacting methanol and carbon monoxide in the presence of a carbonylation catalyst, a catalyst stabilizer, methyl iodide, water and methyl acetate to produce an acetic acid stream comprising acetic acid, water, methyl acetate, methyl iodide, the catalyst, the catalyst stabilizer, and an aldehyde impurity;
(b) flashing at least a portion of the acetic acid stream to produce a vapor stream comprising acetic acid, water, methyl acetate, methyl iodide and the aldehyde impurity, and a liquid stream comprising the catalyst and the catalyst stabilizer;
(c) separating the vapor stream using a distillation column into an acetic acid product stream comprising acetic acid, the aldehyde impurity, and a minor amount of water, and an overhead stream comprising methyl iodide, water, acetic acid, and methyl acetate;
(d) feeding the acetic acid product stream and a hydroxyl compound selected from the group consisting of glycols, glycerin, and $C_{4-10}$ alcohols into a distillation column, wherein the aldehyde impurity reacts with the hydroxyl compound to form an acetal, and wherein the water is removed from a top portion of the distillation column and an essentially anhydrous acetic acid product stream comprising acetic acid and the acetal is taken from the distillation column; and
(e) separating the acetal from acetic acid by distillation.
2. The method of claim 1, wherein the catalyst is a rhodium catalyst.
3. The method of claim 1, wherein the catalyst stabilizer is selected from the group consisting of pentavalent Group VA oxides, metal iodide salts, and mixtures thereof.
4. The method of claim 1, wherein the catalyst stabilizer is a phosphine oxide.
5. The method of claim 1, wherein the catalyst stabilizer is triphenylphosphine oxide.
6. The method of claim 1, wherein the water concentration in step (a) is 10 wt % or less based on the total weight of the acetic acid stream.
7. The method of claim 1, wherein the water concentration in step (a) is 6 wt % or less based on the total weight of the acetic acid stream.
8. The method of claim 1, wherein the hydroxyl compound is a glycol selected from the group consisting of 2-methyl-1,3-propanediol, ethylene glycol, 1,2-propylene glycol, 1,3-propylene glycol, 1,2-butanediol, 1,3-butanediol, 1,5-pentanediol, 1,6-hexanediol, 2,2-dimethyl-1,3-propanediol, cyclohexane-1,4-dimethanol, neopentyl glycol, and mixtures thereof.
9. The method of claim 1, wherein the hydroxyl compound is 2-methyl-1,3-propanediol.
10. The method of claim 1, which comprises recycling the liquid stream of step (b) to the reaction of step (a).
11. The method of claim 1, which comprises condensing and separating the overhead stream of step (c) in a decanter into a light, aqueous phase comprising water, acetic acid, and methyl acetate, and a heavy, organic phase comprising methyl iodide.
12. The method of claim 11, wherein the heavy, organic phase is recycled to the reaction of step (a).
13. The method of claim 11, wherein the light, aqueous phase is recycled to the reaction of step (a) or the distillation of step (c).
14. The method of claim 1, wherein the aldehyde impurity has a boiling point of 75° C. or higher.
15. The method of claim 1, wherein the aldehyde impurity is selected from the group consisting of crotonaldehyde, 2-ethylcrotonaldehyde, 2-ethylbutyraldehyde, and mixtures thereof.
16. The method of claim 1, wherein the aldehyde impurity is crotonaldehyde.

17. The method of claim 1, wherein in step (d), the reaction of the aldehyde impurity with the hydroxyl compound is performed in the presence of a mineral acid.

18. A method for producing acetic acid, said method comprising:
  (a) reacting methanol and carbon monoxide in the presence of a carbonylation catalyst, a catalyst stabilizer, methyl iodide, water and methyl acetate to produce an acetic acid stream comprising acetic acid, water, methyl acetate, methyl iodide, the catalyst, the catalyst stabilizer, and an aldehyde impurity;
  (b) flashing at least a portion of the acetic acid stream to produce a vapor stream comprising acetic acid, water, methyl acetate, methyl iodide and the aldehyde impurity, and a liquid stream comprising the catalyst and the catalyst stabilizer;
  (c) feeding the vapor stream and a hydroxyl compound selected from the group consisting of glycols, glycerin, and $C_{4-10}$ alcohols into a distillation column, wherein the aldehyde impurity reacts with the hydroxyl compound to form an acetal;
  (d) withdrawing an essentially anhydrous acetic acid product stream comprising acetic acid and the acetal from the distillation column; and
  (e) separating the acetal from acetic acid by distillation.

19. The method of claim 18, wherein the aldehyde impurity is selected from the group consisting of acetaldehyde, crotonaldehyde, 2-ethylcrotonaldehyde, butyraldehyde, 2-ethylbutyraldehyde, and mixtures thereof.

20. The method of claim 18, wherein the aldehyde impurity is acetaldehyde.

21. The method of claim 18, wherein in step (c), the reaction of the aldehyde impurity with the hydroxyl compound is performed in the presence of a mineral acid.

22. A method for producing acetic acid, said method comprising:
  (a) reacting methanol and carbon monoxide in the presence of a carbonylation catalyst, a catalyst stabilizer, methyl iodide, water and methyl acetate to produce an acetic acid stream comprising acetic acid, water, methyl acetate, methyl iodide, the catalyst, the catalyst stabilizer, and an aldehyde impurity;
  (b) flashing at least a portion of the acetic acid stream to produce a vapor stream comprising acetic acid, water, methyl acetate, methyl iodide and the aldehyde impurity, and a liquid stream comprising the catalyst and the catalyst stabilizer;
  (c) feeding the vapor stream and a hydroxyl compound into a distillation column, wherein the aldehyde impurity reacts with the hydroxyl compound selected from the group consisting of glycols, glycerin, and $C_{4-10}$ alcohols to form an acetal; and
  (d) withdrawing a heavy stream comprising the acetal from the distillation column.

23. The method of claim 22, which comprises separating the acetal from the heavy stream, disposing the acetal, and recycling the purified heavy stream to the carbonylation of step (a).

24. The method of claim 22, wherein in step (c), the reaction of the aldehyde impurity with the hydroxyl compound is performed in the presence of a mineral acid.

* * * * *